United States Patent [19]

Chau et al.

[11] Patent Number: 5,637,313
[45] Date of Patent: Jun. 10, 1997

[54] CHEWABLE DOSAGE FORMS

[75] Inventors: Tommy L. Chau, Oakdale; Nicholas A. La Bella, Jr., East Setauket, both of N.Y.

[73] Assignee: Watson Laboratories, Inc., Corona, Calif.

[21] Appl. No.: 357,506

[22] Filed: Dec. 16, 1994

[51] Int. Cl.$^6$ .................................................. A61K 9/20
[52] U.S. Cl. ........................ 424/440; 424/469; 424/488
[58] Field of Search ................................ 424/440, 469, 424/488; 514/819, 820; 425/3–6

[56] References Cited

U.S. PATENT DOCUMENTS

| | | |
|---|---|---|
| 4,238,475 | 12/1980 | Witzel et al. . |
| 4,238,510 | 12/1980 | Cherukuri et al. . |
| 4,279,931 | 7/1981 | Verwaerde et al. . |
| 4,317,838 | 3/1982 | Cherukuri et al. . |
| 4,327,076 | 4/1982 | Puglia et al. ................................ 424/38 |
| 4,327,077 | 4/1982 | Puglia et al. . |
| 4,346,116 | 8/1982 | Verwaerde et al. . |
| 4,423,086 | 12/1983 | Devos et al. . |
| 4,528,206 | 7/1985 | Kastin . |
| 4,533,543 | 8/1985 | Morris et al. . |
| 4,545,989 | 10/1985 | Becker et al. . |
| 4,582,707 | 4/1986 | Calabro . |
| 4,609,543 | 9/1986 | Morris et al. . |
| 4,620,982 | 11/1986 | Serpelloni . |
| 4,704,269 | 11/1987 | Korab ...................................... 424/44 |
| 4,738,854 | 4/1988 | Friello et al. . |
| 4,800,095 | 1/1989 | Carroll et al. . |
| 4,867,989 | 9/1989 | Silva et al. . |
| 4,882,152 | 11/1989 | Yang et al. . |
| 4,882,161 | 11/1989 | Scheurer et al. . |
| 4,904,482 | 2/1990 | Patel et al. . |
| 4,933,188 | 6/1990 | Cherukuri et al. . |
| 4,935,243 | 6/1990 | Borkan et al. . |
| 4,946,684 | 8/1990 | Blank et al. . |
| 5,045,340 | 9/1991 | Kohler . |
| 5,075,118 | 12/1991 | DiFalco, Jr. et al. . |
| 5,077,053 | 12/1991 | Kuncewitch et al. . |
| 5,084,298 | 1/1992 | Hussein et al. . |
| 5,120,551 | 6/1992 | Yatka et al. . |
| 5,225,197 | 7/1993 | Bolt et al. . |
| 5,320,848 | 6/1994 | Geyer et al. . |
| 5,324,751 | 6/1994 | DuRoss . |
| 5,330,760 | 7/1994 | Walton . |
| 5,409,907 | 4/1995 | Blase et al. ............................. 514/54 |

OTHER PUBLICATIONS

Roquette Corporation Brochure, "Lycasin® 80/55, Sugarless Excipient for Medicinal Preparations Technical Aspects", 1st printing 10.91, including cover page, summary page, pp. 3–22 and back page.

Roquette Corporation Brochure, "Lycasin®: A multifunctional Ingredient", pp. 1–6.

*Primary Examiner*—Thurman K. Page
*Assistant Examiner*—Sharon Howard
*Attorney, Agent, or Firm*—Darby & Darby

[57] ABSTRACT

Disclosed is a soft, chewable dosage form, including a matrix of hydrogenated starch hydrolysate, a water soluble bulking agent, and a water insoluble bulking agent. The present invention also includes a method of preparing a soft, chewable dosage form, including the steps of mixing under high shear force, a hydrogenated starch hydrolysate, a water soluble bulking agent, and a water insoluble bulking agent until a uniformly blended matrix is obtained. Active ingredients may optionally be incorporated in the matrix.

29 Claims, No Drawings

CHEWABLE DOSAGE FORMS

FIELD OF THE INVENTION

The present invention is directed to a soft, chewable pharmaceutical dosage form. More particularly, the present invention is directed to an oral delivery system for administering a pharmaceutical agent, medicinal or other active ingredient by employing a soft, chewable matrix to incorporate the active ingredient.

BACKGROUND OF THE INVENTION

Pharmaceutical and nutritional supplement dosage forms intended for oral administration are typically provided in solid form as tablets, capsules, pills, lozenges or caplets. The tablet form is swallowed whole, chewed in the mouth, or applied sublingually. Absorption of the active moiety depends upon its release from the dosage form and may be controlled by several different technologies.

Chewable delivery systems are often used in the formulation of pharmaceuticals. Chewable systems are often employed in the administration of pharmaceuticals, where it is impractical to provide a tablet for swallowing whole. The act of chewing increases the surface area of the available active ingredient and may increase the rate of absorption by the digestive tract. Chewable systems are also advantageous where it is desirable to make an active ingredient available topically to the mouth or throat areas for both local effects or systemic absorption. Chewable dosage forms are also utilized to ease drug administration in pediatric and geriatric patients.

Palatability and "mouth feel" are important characteristics to be considered in providing a dosage form, or matrix, for an active pharmaceutical or medicinal. Unfortunately, many pharmaceuticals and other active ingredients have a bitter or otherwise unpalatable taste, or an unacceptable mouth feel, due to the grittiness or chalkiness of the compound, or both. These characteristics make it difficult to incorporate such active ingredients into the current state of the art for chewable dosage forms because the objectionable taste and/or mouth feel make it less likely to obtain compliance by the user.

As a result, several approaches have been tried in attempting to overcome these problems. The poor taste of a pharmaceutical or other active ingredient may be masked by using suitable flavoring compounds and/or sweeteners. Encapsulation of the active ingredient may also serve to mask bitterness and other undesirable tastes. However, these approaches do not affect the physical state of the dosage form currently employed in the art. For example, chewable vitamin tablets are typically prepared as a compressed, compacted tablet, incorporating one or more active ingredients (e.g., vitamins), a sweetener and flavoring agent to mask the taste of the active ingredients, and a binder, typically microcrystalline cellulose.

Generally, chewable tablets are made by direct compression of a mixture of tableting compounds including the active ingredient, flavorant, binders, etc. The mixture is fed into a die chamber of a tablet press and a tablet is formed by direct compaction. Hardness of the resulting tablet is a direct function of the compression pressure employed. A softer tablet, having an easier bite-through, may be prepared by adding a disintegrant, such as alginic acid, to the pre-tablet mix. Alternatively, a softer tablet may be formed by employing reduced compression pressures. In either case, the resultant tablet is softer, fragile, brittle and easily chipped. See U.S. Pat. No. 4,327,076, incorporated herein by reference.

Compressed, chewable tablets generally suffer from less than desirable mouth feel, i.e., chalkiness, grittiness, and a dry, powdery taste. Antacid tablets, e.g., Tums® manufactured by SmithKline Beecham Corp., Pittsburgh, Pa. and Rolaids® manufactured by Warner Lambert of Morris Plains, N.J., are each examples of typical compressed chewable tablets.

Attempts have been made to reduce the grittiness and/or chalkiness of the compressed tablet by coating particles of the active ingredient with oils or fats, which coat the particles prior to incorporation into the delivery system. See U.S. Pat. Nos. 4,327,076 and 4,609,543, incorporated herein by reference. In this way, the grittiness or chalkiness of the particles is masked by the oil or fat while the particles are in the mouth. In addition, tablet softness is improved. After swallowing, the oil or fat is removed and the particle can be absorbed by the digestive system. However, the addition of fats or oils to the pre-tablet mix can cause the tableting ingredients to adhere to the die chamber and cause a reduction in the binding action of the binders present in the mix.

Other techniques for providing a chewable delivery system involve the use of a gum base. Gum bases are insoluble elastomers which form the essential element for chewing gum. The gum base is typically blended with one or more sweeteners to obtain a confectionery gum. A coating containing the active ingredient is then applied over the confectionery gum. As the dosage form is chewed, the coating fractures and/or is dissolved in the mouth and swallowed. This approach is currently employed with gum-based products manufactured by Schering Plough HealthCare, such as aspirin (Aspergum®); antacids (Chooz®); and laxatives (Feenamint®). Dosage forms of this nature (especially aspirin) may not provide the active ingredient as a bioavailable agent to the same extent as an oral tablet dosage form. See "Relative Bioavailability of Aspirin Gum", J. Pharm. Sci., 70:1341 (1981).

Another type of chewable delivery system incorporates the active ingredient into the gum base. Nicotine polacrilex (Nicorette®) distributed by Marion Merrell Dow, is an example of this technology.

Other delivery systems involve the used of layered, non-homogeneous structures.

Another chewable delivery system is based on a nougat-type, chewy tablet. Such tablets generally employ a base of corn syrup (or a derivative). Such tablets are prepared as a confectionery, i.e., the corn syrup is cooked with water and a binder such as soy protein. One example of such a tablet is Tempo® antacid tablets, distributed by Thompson Medical Co., Inc., of West Palm Beach, Fla.

OBJECTS OF THE PRESENT INVENTION

It is an object of the present invention to provide a soft, chewable dosage form which is pliable and chewy, yet dissolves quickly in the mouth, has a long shelf life, contains little moisture which improves stability and decreases the tendency for the dosage form to dry out, does not require cooking or heating as part of the manufacturing process and is preferably non-nutritive. The dosage form may be used as a matrix for an active pharmaceutical ingredient or other medicament. Alternatively, the dosage form may serve as a confectionery or other comestible or a component thereof, including chewing gum.

SUMMARY OF THE INVENTION

The present invention is directed to a soft, chewable dosage form, including a matrix of hydrogenated starch hydrolysate, a water soluble bulking agent, and a water insoluble bulking agent. Active ingredients may optionally be incorporated in the matrix. The present invention also includes a method of preparing a soft, chewable dosage form, including the steps of mixing under high shear force, a hydrogenated starch hydrolysate, a water soluble bulking agent, and a water insoluble bulking agent until a uniformly blended matrix is obtained.

DETAILED DESCRIPTION OF THE INVENTION

According to the present invention, a soft, chewable dosage delivery form is provided. The dosage form may be provided in tablet form and may contain one or more active ingredients to be delivered. The active ingredients are incorporated into a matrix described in further detail below. Alternatively, the matrix may be employed as a major or minor component of a comestible, such as chewing gum.

The matrix of the present invention is prepared by carefully mixing a hydrogenated starch hydrolysate (HSH) with both a water soluble bulking agent and a water insoluble bulking agent. The components of the matrix are mixed using a sigma-bladed mixer (or other high shear mixer), under ambient temperature conditions, and preferably in a low humidity environment. An active ingredient may be incorporated in the matrix during mixing or thereafter. Alternatively, the bulking agent may itself constitute the active ingredient. For example, for antacids, mineral supplements or insoluble active agents, the active ingredient may serve as the water insoluble bulking agent. Likewise, water soluble active ingredients may be used to serve as the water soluble bulking agent. Optionally, flavorants, colorants, encapsulated materials (e.g., encapsulated active ingredients) or other additives may be incorporated into the matrix. Additionally, minor amounts of a humectant, such as glyercin or a glycol, for example, may be added. The present dosage form is a suitable matrix for the incorporation of chewable pharmaceutical and nutritional compounds, and lends itself to easy manufacture, good taste masking, improved texture, and easy manipulation of bioavailability. The dosage form is particularly well suited to the incorporation of encapsulated active ingredients. The microencapsulated active ingredients are usually susceptible to fracture upon application of pressure. Because no direct compaction step is employed (as contrasted with traditional tableting techniques), the microcapsules are not broken during manufacture of the tablet.

Hydrogenated starch hydrolysate is also referred to in the literature as hydrogenated glucose syrup; maltitol or maltitol syrup; Lycasin® polyol, manufactured Roquette Corp, of Gurnee, Ill.; or Lonza® polyol, manufactured by Lonza Fairlawn, N.J. The term hydrogenated starch hydrolysate (or HSH) will be used herein to designate such material. The HSH is usually sold commercially in the form of an aqueous solution thereof having a moisture content of about 15 to 35%.

The preferred HSH has a low moisture content, e.g., less than 25%, and preferably about 15%. A high moisture content makes the matrix wetter and sticky, and requires the addition of increased amounts of water soluble bulking agents to obtain a suitable soft, non-sticky texture for the matrix. This in turn, makes the matrix harder and less pliable.

Water soluble bulking agents which may be employed include any food grade material, including hydrocolloid thickeners and binders, such as gum arabic, pectins, modified starches, alginates, carrageenans, xanthan gums, carboxymethylcellulose, methylcellulose, hydroxyethylcellulose, hydroxypropylcellulose, hydroxypropylmethylcellulose, propylene glycol alginate, polyvinylpyrrolidone (PVP), carboxyvinyl polymers (such as Carbopol®) and polyethylene oxide polymers (such as Polyox®). Preferred water soluble bulking agents include sweeteners such as sorbitol, xylitol, sucrose, fructose, dextrose, mannitol, starch maltodextrin, corn syrup solids, or combinations thereof. Particularly preferred water soluble bulking agents are sorbitol and xylitol.

The water insoluble bulking agent lends both body and structure to the product. Any relatively water insoluble food grade material, insoluble pharmaceutical active ingredient, or insoluble pharmaceutical inactive ingredient may be employed as the water insoluble bulking agent. Examples of suitable water insoluble bulking agents include talc, dicalcium phosphate, powdered celluloses, microcrystalline celluloses and antacid compounds. In the case of celluloses, these agents can also serve as a reinforcing filler.

Antacid compounds are the preferred water insoluble bulking agent when the product is intended as an antacid tablet. Antacid compounds include: aluminum carbonate, aluminum hydroxide (or as aluminum hydroxide-hexitol stabilized polymer, aluminum hydroxide-magnesium hydroxide codried gel, aluminum hydroxide-magnesium trisilicate codried gel, aluminum hydroxide-sucrose powder hydrated), aluminum phosphate, aluminum hydroxy carbonate, dihydroxy aluminum sodium carbonate, aluminum magnesium glycinate, dihydroxy aluminum aminoacetate, dihydroxyaluminum aminoacetic acid, bismuth aluminate, bismuth carbonate, bismuth subcarbonate, bismuth subgallate, bismuth subnitrate, calcium carbonate, calcium citrate, calcium phosphate, hydrated magnesium aluminate activated sulfate, magnesium aluminate, magnesium aluminosilicates, magnesium carbonate, magnesium glycinate, magnesium hydroxide, magnesium oxide and magnesium trisilicate.

Preferred antacids include aluminum hydroxide, calcium carbonate, magnesium carbonates, magnesium hydroxide and mixtures thereof. When the desired product is a mineral supplement, it is preferred to employ a water insoluble bulking agent which includes the desired mineral or minerals. Thus, it is preferred to use calcium carbonate as the water insoluble bulking agent when preparing a calcium supplement tablet. In this case, calcium carbonate serves as both the water soluble bulking agent and the active ingredient.

The relative proportions of the HSH, water soluble bulking agent and water insoluble bulking agent are important to obtaining a suitable matrix. The HSH (15% moisture) should amount to between about 7 and about 45% by weight of the matrix, and preferably between 14 and 27% by weight. The water soluble bulking can account to up to 90% by weight of the matrix, preferably between about 30 and 60% by weight. The water insoluble bulking agent can account for up to about 65% by weight of the matrix, preferably between about 15 and 40%. Minor amounts of flavorants, colorants, glycerin, flavor enhancers, sweeteners, emulsifiers, antibitterness agents, taste masking agents, stabilizers, preservatives, or combinations thereof may be added.

When used as a delivery system, the matrix may incorporate any suitable active ingredient including, but not limited to medicaments, vitamins, mineral supplements and other chemical or biological substances intended for use in the treatment, prevention, diagnosis, cure or mitigation of disease or illness, or substances which affect the structure or function of the body. The present dosage form may be used in either human or veterinary applications.

Suitable categories of drugs that may be employed in the present invention include any stable drug combination. Illustrative categories and specific examples include:

(a) Antitussives, such as dextromethorphan, dextromethorphan hydrobromide, noscapine, carbetapentane citrate, and chlophedianol hydrochloride;

(b) Antihistamines, such as chlorpheniramine maleate, phenindamine tartrate, pyrilamione maleate, doxylamine succinate, and phenyltoloxamine citrate;

(c) Decongestants, such as phenylephrine hydrochloride, phenylpropanolamine hydrochloride, pseudoephedrine, hydrochloride ephedrine;

(d) Various alkaloids, such as codeine phosphate, codeine sulfate and morphine;

(e) Mineral supplements such as potassium chloride and calcium carbonates, magnesium oxide and other alkali metal and alkaline earth metal salts;

(f) Laxatives, vitamins and antacids;

(g) Ion exchange resins such as cholestyramine;

(h) Anti-cholesterolemic and anti-lipid agents such as gemfibrozil;

(i) Antiarrhythmics such as N-acetyl-procainamide;

(j) Antipyretics and analgesics such as acetaminophen, aspirin, ibuprofen and naproxen;

(k) Appetite suppressants such as phenylpropanolamine hydrochloride or caffeine;

(l) Expectorants such as guaifenesin;

(m) Antibiotics such as penicillins, cephalosporins and macrolide antibiotics;

(n) Topical antifungals such as miconazole;

(o) Oral nitrates such as isosorbide dinitrate, isosorbide mononitrate, and nitroglycerin; and (p) Vitamins, alone or in combination, as multi-vitamins.

Additional useful active medicaments include anti-inflammatory substances, coronary dilators, cerebral dilators, peripheral vasodilators, anti-infectives psychotropics, antimanics, stimulants, gastro-intestinal sedatives, antidiarrheal preparations, anti-anginal drugs, vasodilators, anti-hypertensive drugs, vasoconstrictors and migraine treatments, antibiotics, tranquilizers, antipsychotics, antitumor drugs, anticoagulants and antithrombotic drugs, hypnotics, sedatives antiemetics, antinauseants, anticonvulsants, neuromuscular drugs, hyper- and hypoglycemic agents, thyroid and antithyroid preparations, diuretics, antispasmodics, uterine relaxants, nutritional additives, antiobesity drugs, anabolic drugs, erythropoietic drugs, antiasthmatics, cough suppressants, mucolytics, anti-uricemic drugs, and the like. Mixtures of the drugs and medicaments may also be used.

The present matrix may also be used in or as a comestible. The comestible products of the present invention include confectionery products such as chewing gum, including non-bubble gum as well as the bubble gum types, hard candy, liquid filled chewing gum and candy; cough drops, breath fresheners.

The preferred comestible products of the present invention are chewing gum products. The chewing gum compositions contemplated by the present invention comprise all types of sugar and sugarless chewing gums and chewing gum formulations known to those skilled in the art, including regular and bubble gum types. Typical chewing gum compositions comprise a chewing gum base, a modifier, a bulking agent or sweetener, and one or more other additives such as, flavoring agents, colorants and antioxidants. The modifying agents are used to soften, plasticize and/or compatibilize one or more of the components of the gum base and/or of the formulation as a whole.

The following examples are set forth to provide further appreciation of the present invention but are not meant in any way to restrict the scope of the claimed invention.

EXAMPLE 1

An antacid tablet was prepared employing the matrix of the present invention.

611.0 grams of Lycasin-85 HSH syrup, obtained from Roquette Corp, Curnee, Ill.; 866.6 grams of U.S.P. grade $CaCO_3$, obtained from Omya Inc., Proctor, Vt., and 1115.4 grams of food grade sorbitol, obtained from Lonza, Inc., Fairlawn, N.J. were mixed using a 0.75 gallon sigma-bladed, double arm mixer as follows. The Lycasin syrup and one half of the sorbitol were introduced to the sigma-bladed mixer (Baker Perkins), with one arm rotating at 24 rpm and the other at 38 rpm for 1.5 minutes. One half of the $CaCO_3$ was then added and mixed. After the mixture was thoroughly blended (about 1 minute) the remaining $CaCO_3$ was added with continuous mixing. Spearmint flavorant (1.6 grams), green colorant (0.3 grams) and 5.2 grams of glycerin were then introduced. The remaining sorbitol was then gradually added, and the mixing continued until the matrix was thoroughly blended (about 2 minutes). The mixing was conducted at room temperature.

After mixing, the material is allowed to cool to room temperature. It is then rolled to desired thickness and cut into tablets of desired size. Finally, the tablets are waxed and polished.

EXAMPLES 2–11

Tablets were prepared using varying amounts of HSH and soluble and insoluble bulking agents. In addition, different active ingredients and additives were used. The proportions (in percentages by weight) of ingredients and batch sizes are identified in Tables 1 and 2 below.

The procedure used to prepare tablets according to these Examples was as follows:

The HSH solution and approximately one half of the water soluble bulking agent were mixed in the sigma mixer. Glycerin (if used) and other additives (if used) were then added. The mixture was mixed for about 1.5 to 3 minutes or until a uniform paste-like mixture was obtained. The water insoluble bulking agent was then added and the mixing continued for an additional 2 to 4 minutes. The flavorant and color were then added and the mixing continued for another minute or until a uniform mixture was obtained. Finally, the remaining one half of the water soluble bulking agent was added and the mixing continued for another 2 minutes. Because frictional forces in the sigma mixer can cause the temperature to rise to about 30°–35° C. or higher, cooling jackets may be employed to control the temperature when temperature-sensitive active ingredients are employed.

After mixing, the material was allowed to cool to room temperature. It was then rolled to a thickness of about 0.6 cm, and cut into tablets of approximately 1.4×2.0 cm. Finally, the tablets were waxed and polished.

Optionally, a sugar or sugarless coating may be applied to the tablets.

TABLE 1

| Batch Size (in grams) | 2600 | 2400 | 2459 | 2400 | 1800 | 2000 |
|---|---|---|---|---|---|---|
| Example No. | 1 | 2 | 3 | 4 | 5 | 6 |
| HSH-LYCASIN 85% SOLUTION (ROQUETFE CORP, KEOKUK, IA) | 23.50 | 18.00 | 23.262 | 22.50 | 12.00 | 15.00 |
| GLYCERIN (96%) (RUGER, IRVINGTON, N.J.) | 0.2 | | | | | 0.50 |
| CALCIUM CARBONATE, USP, PHAMA-CARB (OMYA INC., PROCTOR, VT) | 33.33 | 37.88 | 40.053 | 37.88 | 37.88 | 37.88 |
| SORBITOL, 60 HI DEX 100, (LONZA, FAIR LAWN, NJ) | 42.90 | 24.566 | | 34.556 | 27.96 | 29.49 |
| SPEARMINT FLAVOR #660, (SCM/GLIDCO, JACKSONVILLE, FL) | 0.06 | | | | | |
| FD&C GREEN COLOR BLEND LB-758, (COLORCON, WEST POINT, PA) | 0.01 | 0.004 | | | | |
| POWDERED CELLULOSE CL-40 (VAN DEN BERGH FOOD, TRUMBULL, CT) | | 1.00 | 1.057 | | | |
| GUM ARABIC POWDER, USP, (GRAYMOR CHEMICAL, ELIZABETH, NJ) | | 2.00 | | | | |
| MINT FLAVOR #279084 (HAARMANN & REIMER, SPRINGFIELD, NJ) | | 0.05 | | | | |
| XYLITOL CM 170 (AMERICAN XYROFIN INC., SCHAUMBURG, IL) | | 16.50 | | | 10.00 | 17.00 |
| GRAPEFRUIT FLAVOR #301-50-1 (GRINDSTED, INDUSTRIAL AIRPORT, KANSAS) | | | 0.211 | | | |
| FD&C RED #40 (COLORCON, WEST POINT, PA) | | | 0.002 | | 0.01 | |
| SUGAR, 6× (DOMINO SUGAR, NEW YORK, NY) | | | 35.415 | | | |
| FD&C BLUE #1 (COLORCON, WEST POINT, PA) | | | | 0.004 | | |
| PEPPERMINT FLAVOR #514 (SCM/GLIDCO, JACKSONVILLE, FL) | | | | 0.06 | | |
| MALTODEXTRIN, MALTRIN M040 (GRAIN PROCESSING CORP., MUSCATINE, IA) | | | | 5.00 | | |
| CHERRY FLAVOR 30-422 (SCM/GLADCO, JACKSONVILLE, FL) | | | | | 0.15 | |
| XYLITOL/ALIGNATE SOLUTION (75% XYLITOL-AMERICAN XYROFIN, SCHAUMBURG, IL; 2.00% KELTONE LV - KELCO, SAN DIEGO, CA; 23.00% DEIONIZED WATER) | | | | | 12.00 | |
| D&C YELLOW #10 (WARNER JENKINS, ST LOUIS, MO) | | | | | | 0.01 |
| LEMON FLAVOR WONF 99-417 (SCM/GLIDCO, JACKSONVILLE, FL) | | | | | | 0.12 |

TABLE 2

| Batch Size (in grams) | 2000 | 1800 | 1800 | 1800 | 2000 |
|---|---|---|---|---|---|
| Example No. | 7 | 8 | 9 | 10 | 11 |
| HSH-LYCASIN 85% SOLUTION (ROQUETTE CORP, KEOKUK, IA) | 21.50 | 21.50 | 26.00 | 21.50 | 21.00 |
| GLYCERIN (96%) (RUGER, IRVINGTON, N.J.) | 0.50 | 0.75 | 0.75 | 0.75 | |
| CALCIUM CARBONATE, USP, PHAMA-CARB (OMYA INC., PROCTOR, VT) | 37.88 | 20.00 | | 35.00 | 15.00 |
| SORBITOL 60, HI DEX 100, (LONZA, FAIR LAWN, NJ) | 29.99 | 50.82 | 54.95 | 40.25 | 36.51 |
| BROWN COLOR BLEND- FD&C YELLOW #6–65%, FD&C RED #40–21%; FD&C BLUE #2–14% (COLORCON, WEST POINT, PA) | | | | | 0.002 |
| ANHYDROUS 100 MESH CAFFEFNE POWDER (BOEHRINGER INGELHEIM, GERMANY) | | | | | 2.27 |
| XYLITOL CM 170 (AMERICAN XYROFIN INC., SCHAUMBURG, IL) | | | | | 25.00 |
| COFFEE FLAVOR #26156 (HAARMANN & REIMER, SPRINGFIELD, NJ) | | | | | 0.20 |
| PEPPERMINT FLAVOR #514 (GLIDCO, JACKSONVILLE, FL) | | | 0.06 | | |
| CHERRY FLAVOR 30-422 (GLIDCO, JACKSONVILLE, FL) | | | | | |
| D&C YELLOW #10 (A.L. WARNER JENKINS, ST LOUIS, MO) | 0.01 | 0.01 | | 0.01 | |
| LEMON FLAVOR WONF 99-417 (GLIDCO, JACKSONVILLE, FL) | 0.12 | 0.10 | | 0.12 | |
| WHETPRO (75%) GLUTEN (ADM/OGILVIE, DECANTER, IL) | 10.00 | | | | |
| SIMETHICONE, USP (PPG MAZER, GURNEE, IL) | | 6.82 | 0.75 | | |
| MAGNESIUM HYDROXIDE, USP (TOMITA, JAPAN) | | | 8.75 | | |
| ALUMINUM HYDROXIDE, USP (TOMITA, JAPAN) | | | 8.75 | | |
| VITAMIN A (PHARMACHEM LAB, S. HACKENSACK, NJ) | | | | 0.88 | |
| VITAMIN $B_{12}$ (PHARMACHEM LAB, S. HACKENSACK, NJ) | | | | 0.79 | |
| VITAMIN $D_3$ (PHARMACHEM LAB, S. HACKENSACK, NJ) | | | | 0.70 | |

What is claimed is:

1. A soft, chewable dosage form, comprising:

a matrix comprising between 7 and 45% by weight hydrogenated starch hydrolysate, up to 90% by weight of a water soluble bulking agent, and up to 65% by weight of a water insoluble bulking agent.

2. The soft, chewable dosage form of claim 1, further comprising an active ingredient supported by said matrix.

3. The dosage form of claim 1, wherein said matrix comprising between about 14 and 27% by weight hydrogenated starch hydrolysate, between about 30 and 60% by weight of a water soluble bulking agent, and between about 15 and 40% of a water insoluble bulking agent.

4. The dosage form of claim 1, wherein said water soluble bulking agent is selected from the group consisting of sorbitol, xylitol, sucrose, fructose, dextrose, mannitol, starch, maltodextrin, corn syrup solids and mixtures thereof.

5. The dosage form of claim 1, wherein said water insoluble bulking agent is selected from the group consisting of aluminum hydroxide, calcium carbonate, magnesium carbonate, magnesium hydroxide and mixtures thereof.

6. The dosage form of claim 1, wherein said water soluble bulking agent is sorbitol and said water insoluble bulking agent is calcium carbonate.

7. The dosage form of claim 1, wherein the dosage form is selected from the group consisting of tablets, caplets and pills.

8. The dosage form of claim 1, further comprising a flavoring agent.

9. The dosage form of claim 1, further comprising a colorant.

10. The dosage form of claim 1, further comprising a humectant.

11. The dosage form of claim 10, wherein said humectant is glycerin.

12. The dosage form of claim 2, wherein said active ingredient is selected from the group consisting of magnesium hydroxide, aluminum hydroxide, caffeine, simethicone, vitamin A, vitamin $B_{12}$, vitamin $D_3$ and mixtures thereof.

13. A soft, chewable calcium tablet, comprising a matrix comprising between 7 and 45% by weight hydrogenated starch hydrolysate, up to 90% by weight of sorbitol and up to 65% by weight of calcium carbonate.

14. The tablet of claim 13, wherein said tablet is formed from a matrix comprising between about 20 and 25% by weight hydrogenated starch hydrolysate, between about 35 and 45% by weight of sorbitol and between about 30 and 40% of calcium carbonate.

15. A method of preparing a soft, chewable dosage form, comprising the steps of:

mixing under high shear force, between 7 and 45% by weight hydrogenated starch hydrolysate, up to 90% by weight of a water soluble bulking agent, and up to 65% by weight of a water insoluble bulking agent until a uniformly blended matrix is obtained; and forming said matrix into said dosage form.

16. The method of claim 15, wherein said high shear force is provided by a sigma-bladed mixer.

17. The method of claim 15, further comprising the step of adding an active ingredient during the mixing step.

18. The method of claim 15, wherein said mixing takes place in the absence of added heat.

19. The method of claim 15, wherein said matrix is rolled to a predetermined thickness and cut into tablets of predetermined size.

20. A soft, chewable antacid tablet, comprising a matrix comprising between 14 and 27% by weight hydrogenated starch hydrolysate, between 30 and 60% by weight sorbitol, aluminum hydroxide, magnesium hydroxide and simethicone.

21. The dosage form of claim 1, wherein the matrix is non-compressed.

22. The dosage form of claim 2, wherein the matrix is non-compressed.

23. The tablet of claim 13, wherein said matrix is non-compressed.

24. The method of claim 15, wherein said matrix is formed into said dosage form without compression.

25. The method of claim 17, wherein said active ingredient is microencapsulated.

26. The dosage form of claim 2, wherein said active ingredient is microencapsulated.

27. The dosage form of claim 22, wherein said active ingredient is microencapsulated.

28. The dosage form of claim 1 further comprising an emulsifier.

29. The dosage form of claim 1 wherein said dosage form is a comestible.

\* \* \* \* \*